(12) United States Patent
Kuczynski et al.

(10) Patent No.: US 7,338,499 B1
(45) Date of Patent: Mar. 4, 2008

(54) HIP ARTHROPLASTY BALANCING APPARATUS AND METHOD

(75) Inventors: John D. Kuczynski, Pequannock, NJ (US); John R. Simpson, Lodi, NJ (US)

(73) Assignee: Howmedia Osteonics Corp., Mahwah, NJ (US)

( * ) Notice: Subject to any disclaimer, the term of this patent is extended or adjusted under 35 U.S.C. 154(b) by 414 days.

(21) Appl. No.: 10/939,789

(22) Filed: Sep. 13, 2004

(51) Int. Cl.
*A61B 17/58* (2006.01)
(52) U.S. Cl. ..................................... 606/102
(58) Field of Classification Search .............. 606/99, 606/102
See application file for complete search history.

(56) References Cited

U.S. PATENT DOCUMENTS

| | | | |
|---|---|---|---|
| 4,566,448 | A | 1/1986 | Rohr, Jr. |
| 5,116,338 | A | 5/1992 | Poggie et al. |
| 5,213,112 | A | 5/1993 | Niwa et al. |
| 5,540,696 | A | 7/1996 | Booth, Jr. et al. |
| 5,569,263 | A | 10/1996 | Hein |
| 5,800,554 | A | 9/1998 | Scholz |
| 5,911,723 | A | 6/1999 | Ashby et al. |
| 6,193,758 | B1 * | 2/2001 | Huebner ............... 623/19.14 |
| 6,197,065 | B1 | 3/2001 | Martin et al. |
| 2005/0080428 | A1 * | 4/2005 | White .................. 606/102 |
| 2006/0155295 | A1 * | 7/2006 | Supper et al. ............ 606/90 |
| 2006/0217737 | A1 * | 9/2006 | Iversen .................. 606/102 |

OTHER PUBLICATIONS

Keggi Orthopaedic Foundation, Yale Univ. School of Med. Dept. of Orthopaedics & Rehab. Total Hip Arthroplasty Using the Minimally Invasive Anterior Surgical Approach, undated.
Stryker Howmedica Osteonics. "Surgical Technique, Achieving Perfect Balance, Accolade," undated.

* cited by examiner

*Primary Examiner*—Eduardo C. Robert
*Assistant Examiner*—Michael J Araj
(74) *Attorney, Agent, or Firm*—Arthur Jacob (57) ABSTRACT

Apparatus and method for interoperatively determining, during a trialing procedure conducted in connection with total hip arthroplasty at an implant site, a femoral neck length required in a femoral component to be engaged with an acetabular component of the prosthetic hip joint to be implanted at the implant site for establishing forces appropriate for proper articular engagement of the femoral component with the acetabular component, by moving a trial femoral head component and a trial femoral stem component relative to one another, while the trial femoral head component is engaged with an acetabular trial, to determine a measured distance corresponding to a trial distance between the trial femoral head component and the trial femoral stem component at which trial distance selected tensile forces are established in soft tissue at the implant site urging the trial femoral head component and the trial femoral stem component toward one another, the selected tensile forces corresponding to the forces appropriate for proper articular engagement of the femoral component with the acetabular component of the prosthetic hip joint, the trial distance corresponding to the required femoral neck length.

29 Claims, 4 Drawing Sheets

HIP ARTHROPLASTY BALANCING APPARATUS AND METHOD

The present invention relates generally to hip arthroplasty and pertains, more specifically, to apparatus and method for balancing forces exerted upon a hip prosthesis by soft tissue at a hip implant site.

Total hip arthroplasty requires the preparation of an implant site for the reception of a femoral component and an acetabular component of a prosthetic hip joint to be implanted at the implant site. Most total hip prostheses rely upon soft tissue at the implant site, between the pelvis and the proximal femur, to maintain the femoral head provided by the femoral component appropriately engaged with a bearing member of the acetabular component. It becomes essential that the soft tissue be tensioned properly to attain the forces necessary for such appropriate engagement. Too little force can lead to impaired performance and, in particular, ready dislocation of the prosthetic joint. Too great a force can cause premature wear of bearing surfaces, pain, and a reduced range of motion.

An effective balance of these soft tissue forces is achieved through the selection of an appropriate effective length for the neck of the femoral component of the prosthetic joint. That is, the distance between the stem of the femoral component and the femoral head of the component, provided by the effective length of the neck of the component, establishes the requisite tension in the soft tissue which, in turn, provides the forces necessary to maintain the desired articular engagement of the femoral head within the bearing member. Accordingly, of utmost importance is the ability to determine the appropriate neck length with precision, and to do so with ease and assurance. The appropriate length required for the neck of a femoral component is determined once the size of each of the femoral component and the acetabular component is selected, and the implant site is prepared for the reception of each selected component. A preliminary assessment can be made utilizing radiographic analysis; however, a final determination usually is accomplished during the course of the implant procedure itself, that is, interoperatively.

In a current trialing procedure, serial trial prostheses are used to determine the appropriate neck length for soft tissue balance during the conduct of total hip arthroplasty. Thus, a provisional trial prosthesis is put into place, the hip joint is reduced, and the leg of the patient is moved by a surgeon through a range of motion to determine soft tissue balance, by hand, and to check for dislocation. The surgeon also manually distracts the hip joint by pulling on the leg to gain a measure of the forces established in the soft tissue. The trialing procedure requires that the trial prosthesis be removed and replaced with another in a series of trial prostheses in order to evaluate different neck lengths. To achieve a correct balance, a surgeon may need to perform several iterations, each requiring replacement of one trial prosthesis with another in the series, reduction of the hip joint, movement through a range of motion, and then dislocation of the joint again in order to change trials. The procedure can be quite time-consuming and even physically challenging, especially with larger patients. Moreover, the procedure is not suited to the conduct of more recently developed minimally invasive total hip arthroplasty where access to the hip joint is more limited. Further, the procedure provides only a qualitative evaluation of the forces established by different neck lengths. Thus, a surgeon evaluates tension in the soft tissue through manual feel as a patient's leg is manipulated by the surgeon, requiring experience on the part of the surgeon in order to know the correct feel, thereby introducing variations from surgeon to surgeon and concomitant uncertainties.

The present invention provides apparatus and method by which the appropriate effective length for the neck of a femoral component of a prosthetic hip joint is determined interoperatively with ease and with accuracy, for optimal soft tissue tensioning and force balancing. As such, the present invention attains several objects and advantages, some of which are summarized as follows: Facilitates an interoperative determination of the appropriate neck length for a femoral component in a total hip arthroplasty; enables an interoperative quantitative measurement of the tension established in soft tissue at a prosthetic hip implant site as a result of a measured neck length in the femoral component of the prosthetic hip joint, thereby attaining optimal soft tissue tensioning and force balancing at the joint; allows selective changes in the distance between the femoral stem of a femoral trial for a prosthetic hip joint and a femoral head of the femoral trial for interoperatively determining an appropriate effective length of the neck of the femoral component of the prosthetic hip joint itself, without the necessity for serial trial replacements and concomitant multiple dislocations of the hip joint; enables interoperative quantitative measurements of distances, and the forces resulting from such distances, at a hip implant site for consistent, precision results attained with ease and in less time; improves accuracy in the completion of a total hip arthroplasty; facilitates the conduct of minimally invasive total hip arthroplasty, where access to the hip joint is more limited; attains consistent and repeatable results in establishing appropriate soft tissue tension and concomitant balanced forces at hip implant sites with quantitative verification, as opposed to relatively arbitrary qualitative assessments; reduces pain and discomfort, as well as recovery time, in patients subjected to total hip arthroplasty.

The above objects and advantages, as well as further objects and advantages, are attained by the present invention which may be described briefly as an apparatus for interoperatively determining, during a trialing procedure conducted in connection with total hip arthroplasty at an implant site, a femoral neck length required along a predetermined direction in a femoral component to be engaged with an acetabular component in a prosthetic hip joint to be implanted at the implant site for establishing forces appropriate for proper articular engagement of the femoral component with the acetabular component, by determining a measured distance corresponding to a trial distance between a trial femoral head component and a trial femoral stem component of a femoral trial placed at the implant site with the trial femoral head component engaged with an acetabular trial, at which trial distance soft tissue at the implant site is tensioned to establish selected tensile forces in the soft tissue for urging the trial femoral head component into engagement with the acetabular trial, the selected tensile forces corresponding to the forces appropriate for proper articular engagement of the femoral component with the acetabular component, and the trial distance corresponding to the required femoral neck length, the apparatus comprising: a connecting arrangement for connecting the trial femoral head component with the trial femoral stem component for selective movement relative to one another in the femoral trial, during the trialing procedure, along a direction of movement corresponding to the predetermined direction of the femoral neck length; a distance indicator for indicating measured distances corresponding to trial distances between the trial femoral head component and the trial femoral stem component along the direction of movement during the trialing procedure; and a force applier for coupling with the femoral trial to apply selected forces urging the trial femoral head component and the trial femoral stem component away from one another at measured distances indicated by the distance indicator such that upon coupling of the force applier with the femoral trial and applying the selected forces while the trial femoral head component is engaged with the acetabular trial to urge the trial femoral head component and the trial femoral stem component away from one another and tension the soft tissue during the trialing procedure, a measured distance corresponding to a trial distance at which the selected tensile forces are established in the soft tissue is determined interoperatively, thereby determining interoperatively the femoral neck length required in the femoral component for establishing the forces appropriate for proper articular engagement of the femoral component with the acetabular component.

In addition, the present invention provides an apparatus for interoperatively determining, during a trialing procedure conducted in connection with total hip arthroplasty at an implant site, a femoral neck length required along a predetermined direction in a femoral component to be engaged with an acetabular component in a prosthetic hip joint to be implanted at the implant site for establishing forces appropriate for proper articular engagement of the femoral component with the acetabular component, by determining a measured distance corresponding to a trial distance between a trial femoral head component and a trial femoral stem component of a femoral trial placed at the implant site with the trial femoral head component engaged with an acetabular trial, at which trial distance soft tissue at the implant site is tensioned to establish selected tensile forces in the soft tissue for urging the trial femoral head component into engagement with the acetabular trial, the selected tensile forces corresponding to the forces appropriate for proper articular engagement of the femoral component with the acetabular component, and the trial distance corresponding to the required femoral neck length, the apparatus comprising: a connecting arrangement for connecting the trial femoral head component with the trial femoral stem component for selective movement relative to one another in the femoral trial, during the trialing procedure, along a direction of movement corresponding to the predetermined direction of the femoral neck length, while the trial femoral head component is engaged with the acetabular trial, to tension the soft tissue and determine, interoperatively, a measured distance corresponding to a trial distance at which the selected tensile forces are established in the soft tissue, thereby determining, interoperatively, the femoral neck length required in the femoral component for establishing the forces appropriate for proper articular engagement of the femoral component with the acetabular component.

Further, the present invention provides a method for interoperatively determining, during a trialing procedure conducted in connection with total hip arthroplasty at an implant site, a femoral neck length required along a predetermined direction in a femoral component to be engaged with an acetabular component in a prosthetic hip joint to be implanted at the implant site for establishing forces appropriate for proper articular engagement of the femoral component with the acetabular component, by determining a measured distance corresponding to a trial distance between a trial femoral head component and a trial femoral stem component of a femoral trial placed at the implant site with the trial femoral head component engaged with an acetabular trial, at which trial distance soft tissue at the implant site is tensioned to establish selected tensile forces in the soft tissue for urging the trial femoral head component into engagement with the acetabular trial, the selected tensile forces corresponding to the forces appropriate for proper articular engagement of the femoral component with the acetabular component, and the trial distance corresponding to the required femoral neck length, the method comprising: connecting the trial femoral head component with the trial femoral stem component for selective movement relative to one another in the femoral trial, during the trialing procedure, along a direction of movement corresponding to the predetermined direction of the femoral neck length; applying selected forces for selectively moving the trial femoral head component and the trial femoral stem component relative to one another among trialing distances along the direction of movement, while the trial femoral head component is engaged with the acetabular trial during the trialing procedure; and measuring distances corresponding to the trialing distances to determine a measured distance corresponding to a trialing distance at which an applied selected force tensions the soft tissue to establish the selected tensile forces in the soft tissue, thereby determining interoperatively the femoral neck length required in the femoral component for establishing the forces appropriate for proper articular engagement of the femoral component with the acetabular component.

The invention will be understood more fully, while still further objects and advantages will become apparent, in the following detailed description of preferred embodiments of the invention illustrated in the accompanying drawing, in which.

Figure 1:
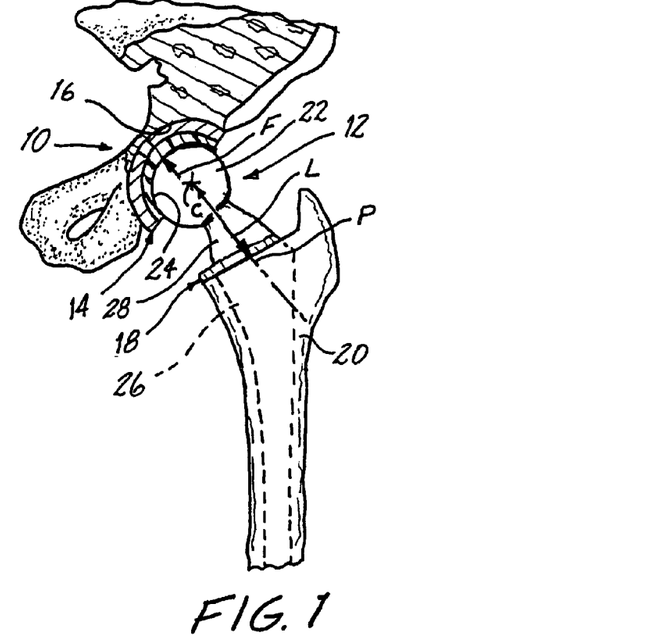
FIG. 1 is a pictorial illustration, somewhat diagrammatic, of a prosthetic hip joint implanted at an implant site.

Referring now to the drawing, and especially to FIG. 1 thereof, an implant site 10 has been provided with a prosthetic hip joint 12 which is seen to include an acetabular component 14 implanted in acetabulum 16, and a femoral component 18 implanted in proximal femur 20. Femoral component 18 includes a femoral head 22, which is engaged with a bearing surface 24 of the acetabular component 14 for articulation of the prosthetic hip joint 12, a femoral stem 26, which is affixed within the proximal femur 20 to secure the femoral component 18 in place, and a femoral neck 28, which connects the femoral head 22 to the femoral stem 26 and which spaces the femoral head 22 from the femoral stem 26, all as now well-known in prosthetic hip joints.

As is conventional, prosthetic hip joint 12 relies upon soft tissue (not shown) at the implant site 10 to maintain femoral head 22 of femoral component 18 appropriately engaged with bearing surface 24 of acetabular component 14 throughout articulation of the prosthetic hip joint 12. Requisite appropriate forces, as represented by force F in FIG.

1, are established by tensioning the soft tissue to a degree of tension which provides the necessary force F. The degree of tension attained in the soft tissue is dependent upon the distance between the femoral head 22 and the femoral stem 26 provided by the femoral neck 28, as represented by the length L which extends along a predetermined direction P between the center of rotation C femoral head 22 and the femoral stem 26. Appropriate force F is attained by selecting a length L which tensions the soft tissue to a requisite tension for establishing tensile forces providing the necessary force F. Accordingly, in order to optimize articular engagement between the femoral head 22 and the bearing surface 24, length L must be selected with precision.

Figure 2:
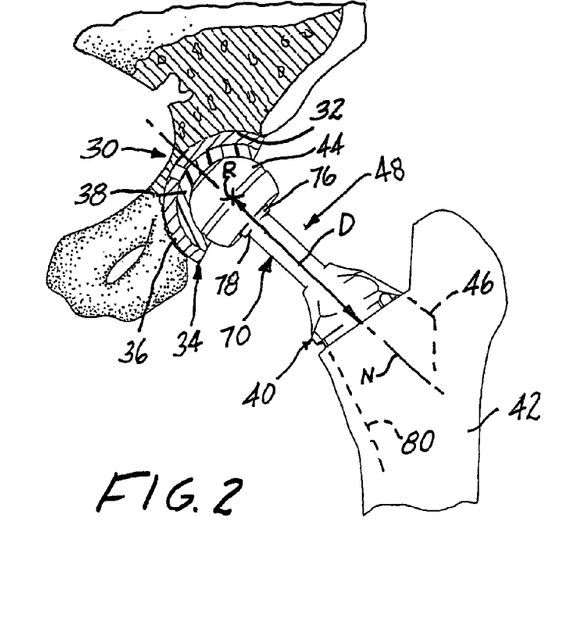
FIG. 2 is a pictorial illustration, somewhat diagrammatic, of a component of apparatus constructed in accordance with the present invention, placed at an implant site during the conduct of a total hip arthroplasty.

Turning now to FIG. 2, an implant site 30 has been prepared for a prosthetic hip implant during the course of a total hip arthroplasty. Acetabulum 32 has been provided with an acetabular trial, shown in the form of acetabular trial 34 including a trial acetabular shell 36 placed within the acetabulum 32 and a trial bearing 38 seated within the trial acetabular shell 36. A femoral trial 40 has been placed within proximal femur 42 and includes a trial femoral head component 44 shown, in a diagrammatic illustration, engaged within trial bearing 38, and a trial femoral stem component 46, simulating, in a trial hip joint 48, the engagement of a femoral component with an acetabular component of a prosthetic hip joint to be implanted at the implant site 30. Appropriate engagement between the femoral component and the acetabular component of the implanted prosthetic hip joint is to be maintained by forces established by tension in the soft tissue at the implant site 30, and it becomes essential that tensile forces in the soft tissue be balanced appropriately so as to establish the forces necessary for maintaining appropriate articular engagement between the femoral component and the acetabular component throughout the full range of motion of the prosthetic hip joint. Tension in the soft tissue at the implant site 30, upon completion of the total hip arthroplasty, is a function of the length of the neck of the femoral component of the prosthetic hip joint implanted at the implant site 30. Accordingly, it becomes of utmost importance that the length of the neck be determined with accuracy.

A trial distance between the center of rotation R of trial femoral head component 44 and the trial femoral stem component 46 of femoral trial 40 is shown at D, along a predetermined direction N, the trial distance D corresponding to the length of the neck of the femoral component of the prosthetic hip joint to be implanted at the implant site 30, as illustrated by way of example as length L along predetermined direction P in femoral component 18 of FIG. 1. A change in the trial distance D results in a corresponding change in the tension in the soft tissue, and a concomitant change in the forces maintaining the engagement between the trial femoral head component 44 and the trial bearing 38. The present invention provides for the selective adjustment of distance D, interoperatively, so as to attain an optimal balance of forces through establishing requisite predetermined tensile forces in the soft tissue for establishing appropriate forces urging and maintaining the femoral trial 40 in proper engagement with the acetabular trial 34.

Figures 3, 4:
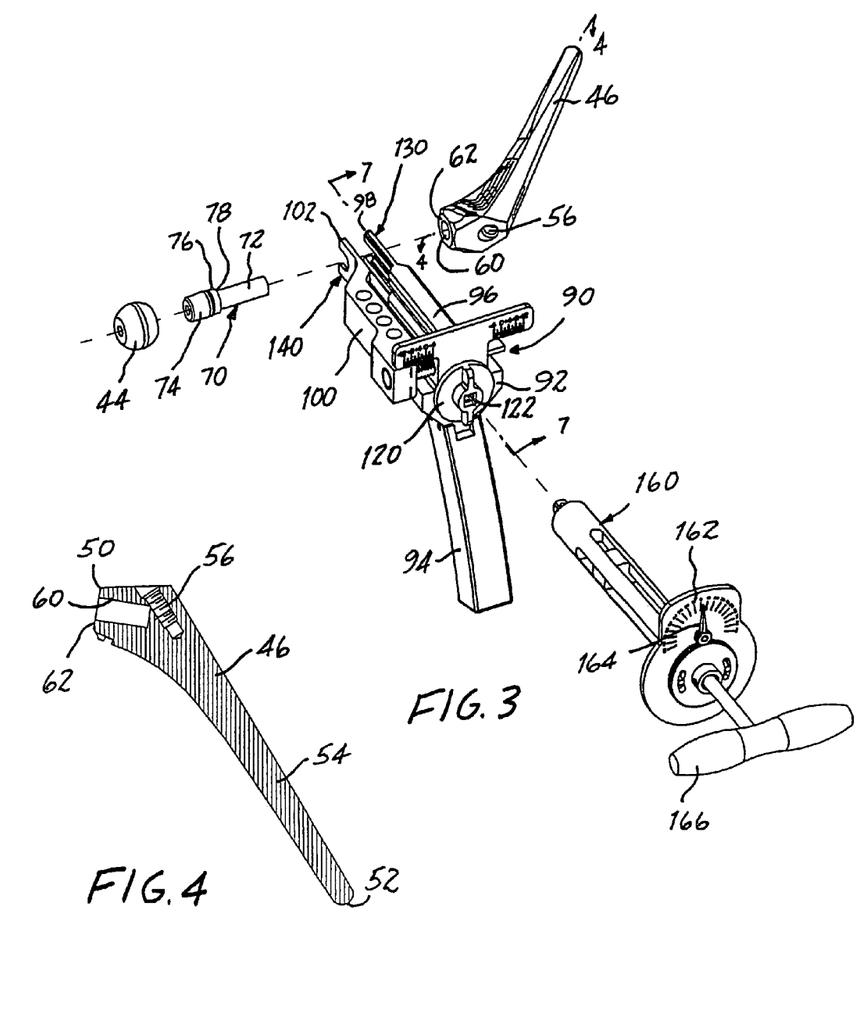
FIG. 3 is an exploded perspective view of the apparatus.
FIG. 4 is a longitudinal cross-sectional view taken alone line 4-4 of FIG. 3.

Referring now to FIGS. 3 and 4, as well as to FIG. 2, the trial femoral stem component 46 of femoral trial 40 extends between a proximal end 50 and a distal end 52. A stem 54 extends from the distal end 52 toward the proximal end 50, and, as best seen in FIG. 4, a threaded hole 56 extends into the trial femoral stem component 46 at the proximal end 50, for purposes to be described below. The trial femoral head component 44 is connected with the trial femoral stem component 46 with a connecting arrangement which includes a passage shown in the form of cylindrical bore 60 extending into the femoral trial stem component 46 from a first reference surface, in the form of stem reference surface 62 at the proximal end 50, and a trial neck 70 which includes a shaft 72 extending longitudinally along a distal portion of the trial neck 70, the shaft 72 being dimensioned and configured for longitudinal sliding engagement within bore 60 so that the trial neck 70 is movable relative to the trial femoral stem component 46 in longitudinal directions. A post 74 extends longitudinally along a proximal portion of the trial neck 70, and a shoulder 76 extends laterally across the trial neck 70, intermediate the shaft 72 and the post 74, and carries a second reference surface in the form of a head reference surface 78. The trial femoral head component 44 selectively is seated upon post 74, in a manner now conventional in the use of trial femoral heads, for placement just proximal of the shoulder 76.

Figure 5:
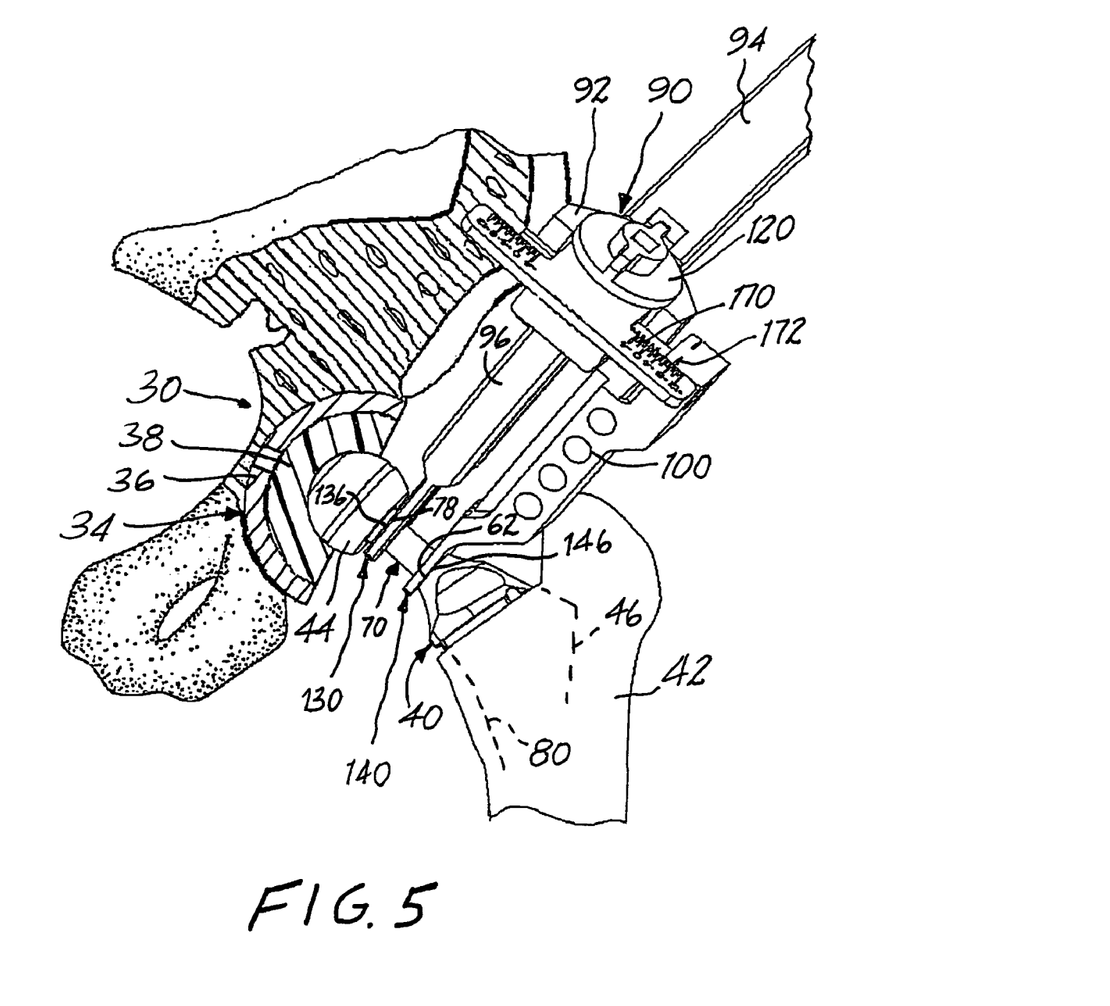
FIG. 5 is a pictorial illustration similar to FIG. 2 and showing components of the apparatus, with the apparatus in use in accordance with a method of the present invention.

Femoral trial 40 is assembled for use by inserting shaft 72 of trial neck 70 into bore 60 of trial femoral stem component 46, and seating trial femoral head component 44 on post 74 of trial neck 70. Stem 54 then is inserted into a prepared cavity 80 in proximal femur 42, as seen in FIG. 5, using conventional techniques, and the hip joint is reduced to place the trial femoral head component 44 into engagement with the trial bearing 38 of the acetabular trial 34, as illustrated in FIG. 5. Once the trial femoral head component 44 is seated within the trial bearing 38, a component of the apparatus in the form of a balancing implement 90 is engaged with the femoral trial 40 for effecting relative movement between the trial femoral head component 44 and the trial femoral stem component 46 for selectively changing the trial distance D between the trial femoral head component 44 and the trial femoral stem component 46 of femoral trial 40, thereby moving the trial femoral head component 44 and the trial femoral stem component 46 relative to one another among different trial distances D along the predetermined distance N.

Figures 6, 7, 8:
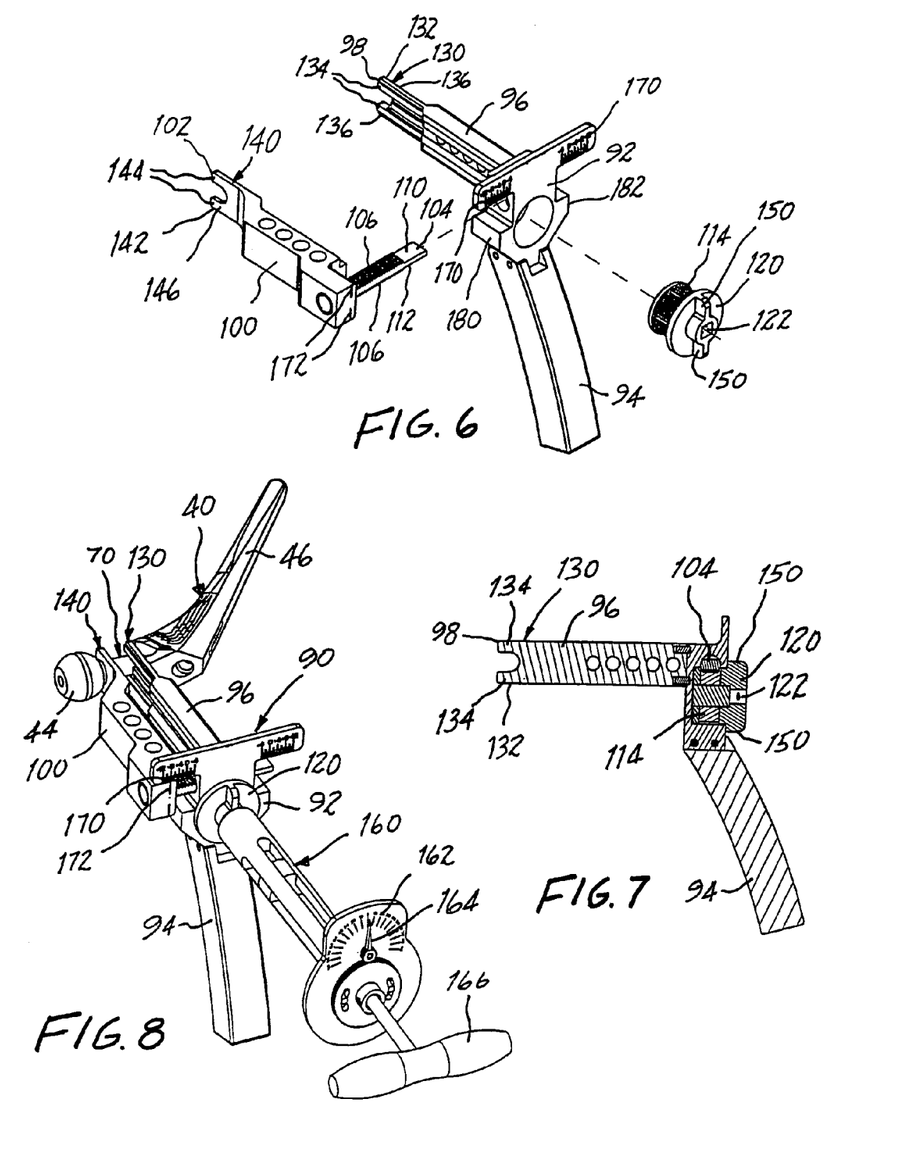
FIG. 6 is an exploded perspective view of a component of the apparatus.
FIG. 7 is a cross-sectional view taken along line 7-7 of FIG. 3.
FIG. 8 is a pictorial perspective view of the apparatus.

Referring now to FIGS. 3, 6 and 7, as well as to FIG. 5, balancing implement 90 includes a frame 92 which carries a hand-grip 94 and a first member in the form of a first arm 96 affixed to the frame 92 and extending laterally from the frame 92 to a first terminal end 98. A second member in the form of a second arm 100 is mounted on the frame 92 and extends laterally from the frame 92 to a second terminal end 102. Second arm 100 carries a longitudinally extending rack 104 adjacent the frame 92, the rack 104 having a series of rack teeth 106 placed along each of altitudinally opposite rack faces 110 and 112. Rack 104 is engaged with a pinion 114 journaled within frame 92 and is movable in longitudinal directions, along a linear path, relative to frame 92, in response to rotation of the pinion 114, the rack 104 and pinion 114 comprising a drive mechanism for selective movement of the second arm 100 in longitudinal directions relative to the first arm 96. An actuator in the form of a knob 120 is affixed to the pinion 114 for enabling rotation of the pinion 114 and concomitant longitudinal displacement of the rack 104 and the second arm 100 relative to the first arm 96. A drive socket 122 is located in knob 120, for purposes to be described hereinafter.

First arm 96 has a first engagement element 130 adjacent terminal end 98, the first engagement element 130 including a bifurcate section 132 having parallel tines 134 and first engagement faces 136. Second arm 100 has a second engagement element 140 including a bifurcate section 142 having parallel tines 144 and a second engagement face 146. As seen in FIG. 8, with reference to FIGS. 3 and 6, balancing implement 90 is coupled with femoral trial 40 by slipping the first and second engagement elements 130 and 140 over the trial neck 70, with the tines 134 and 144 straddling the shaft 72 of the trial neck 70. The knob 120 then is rotated, as facilitated by finger purchases 150, to engage a corresponding first engagement face 136 with the stem reference surface 62 on the trial femoral stem component 46, thereby coupling the first arm 96 with the trial femoral stem component 46, and to engage the second engagement face 146 with the head reference surface 78 on the trial neck 70, thereby coupling the second arm 100 with the trial femoral head component 44. Alternately, as seen in FIG. 5, balancing implement 90 can be coupled with femoral trial 40 by coupling the first arm 96 with the trial femoral head component 44 and coupling the second arm 100 with the trial femoral stem component 46, in which case a corresponding first engagement face 136 is engaged with head reference surface 78 on the trial neck 70, and second engagement face 146 is engaged with stem reference surface 62 on the trial femoral stem component 46.

With the balancing implement 90 coupled to the femoral trial 40, as seen in either FIG. 5 or in FIG. 8, and with the femoral trial 40 engaged with the acetabular trial 34, torque is applied to the knob 120, by a force applier, to change the distance D, along the predetermined direction N, by virtue of the sliding engagement between the shaft 72 and the bore 60, such that the trial femoral head component 44 and the trial femoral stem component 46 are moved relative to one another among different trial distances D, along direction N, and corresponding resultant distraction of the joint will tension the soft tissue at the implant site 30. Distance D is changed until a tension is reached where appropriate tensile forces are established in the soft tissue at the implant site 30. At the same time, the distance D is measured to provide an indication of the neck length necessary for establishing the appropriate tensile forces and the concomitant forces necessary to maintain optimal articular engagement between the femoral trial 40 and the acetabular trial 34.

In order to facilitate the application of sufficient torque to knob 120, the force applier includes a torque wrench 160 which is coupled with drive socket 122 in knob 120, as seen in FIG. 8, to couple the force applier with the drive mechanism provided by rack 104 and pinion 114. Upon operation of the torque wrench 160, through rotation of a handle 166, a force is applied to displace second arm 100 relative to the first arm 96. In the illustrated preferred embodiment, the torque wrench 160 includes a force indicator in the form of dial 162 and pointer 164 so that the magnitude of the applied force is indicated by the dial 162 and pointer 164. The magnitude of the force, as indicated by the dial 162 and pointer 164, is a measure of the forces urging the second arm 100 away from the first arm 96, and corresponds to the magnitude of forces exerted by the soft tissue upon the engaged femoral trial 40 and acetabular trial 34, and is related directly to the tensile forces desired in the soft tissue so that accurate tensioning, and concomitant accurate balancing of tensile forces in the soft tissue, is read directly by reading the force indicator. Thus, tensioning to obtain requisite tensile forces is attained by applying a force of selected magnitude, as measured by, and indicated by, the force indicator, such that the selected force is verified quantitatively, with repeatable accuracy, for quickly attained, precision results. However, a reliable qualitative measure of the applied torque is available to a surgeon by means of feedback through handle 166 of torque wrench 160, and the surgeon may decide that his qualitative determination of tensile force, through the utilization of balancing implement 90 to change distance D, is sufficient to apply a force of selected magnitude, and that he does not require the quantitative verification provided by the force indicator.

At the same time, the displacement of second arm 100, as a result of longitudinal movement relative to the first arm 96, provides an indication of distance D at a distance indicator in the form of a scale 170 on frame 92 and an index 172 carried by second arm 100. In this manner, a surgeon is provided with a direct measurement of a measured distance corresponding to a trial distance D required to attain the predetermined necessary tension in the soft tissue. Once the trial distance D is known, the appropriate neck length has been determined and the balancing implement 90 is uncoupled from the femoral trial 40. It is noted that the balancing implement 90 is constructed to be symmetrical in that the second arm 100 may be uncoupled from the left side 180 of the frame 92, as viewed in FIG. 6, and then coupled to the right side 182 of the frame 92 so as to enable use of the balancing implement 90 in connection with either left or right total hip arthroplasty. To this end, duplicate scales 170 and duplicate indices 172 are provided at the respective sides 180 and 182 of frame 92.

Subsequent to determining the appropriate neck length and uncoupling of the balancing implement 90, the joint is dislocated and the femoral trial 40 is extracted, with the assistance of a conventional extraction instrument which can be coupled to the threaded hole 56 of the trial femoral stem component 46. An appropriate acetabular component and femoral component then are implanted at the implant site 30. Prior to uncoupling balancing implement 90 from femoral trial 40, range of motion and soft tissue tension may be evaluated manually by locking the first and second arms 96 and 100 against further relative movement. Ultimately, an appropriate femoral head prosthesis is assembled with the implanted femoral stem component, the joint is reduced, and a final range of motion and tension evaluation is conducted manually, prior to completion of the implant procedure.

It will be seen that the present invention attains the several objects and advantages summarized above, namely: Facilitates an interoperative determination of the appropriate neck length for a femoral component in a total hip arthroplasty; enables an interoperative quantitative measurement of the tension established in soft tissue at a prosthetic hip implant site as a result of a measured neck length in the femoral component of the prosthetic hip joint, thereby attaining optimal soft tissue tensioning and force balancing at the joint; allows selective changes in the distance between the femoral stem of a femoral trial for a prosthetic hip joint and a femoral head of the femoral trial for interoperatively determining an appropriate effective length of the neck of the femoral component of the prosthetic hip joint itself, without the necessity for serial trial replacements and concomitant multiple dislocations of the hip joint; enables interoperative quantitative measurements of distances, and the forces resulting from such distances, at a hip implant site for consistent, precision results attained with ease and in less time; improves accuracy in the completion of a total hip arthroplasty; facilitates the conduct of minimally invasive total hip arthroplasty, where access to the hip joint is more limited; attains consistent and repeatable results in establishing appropriate soft tissue tension and concomitant balanced forces at hip implant sites with quantitative verification, as opposed to relatively arbitrary qualitative assessments; reduces pain and discomfort, as well as recovery time, in patients subjected to total hip arthroplasty.

It is to be understood that the above detailed description of preferred embodiments of the invention are provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for interoperatively determining, during a trialing procedure conducted in connection with total hip arthroplasty at an implant site, a femoral neck length required along a predetermined direction in a femoral component to be engaged with an acetabular component in a prosthetic hip joint to be implanted at the implant site for establishing forces appropriate for proper articular engagement of the femoral component with the acetabular component, the apparatus comprising:

a femoral trial for placement at the implant site, the femoral trial including a trial femoral head component and a trial femoral stem component, the femoral neck length being determined by determining a measured distance corresponding to a trial distance between the trial femoral head component and the trial femoral stem component of the femoral trial when the femoral trial is placed at the implant site with the trial femoral head component engaged with an acetabular trial, at which trial distance soft tissue at the implant site is tensioned to establish selected tensile forces in the soft tissue for urging the trial femoral head component into engagement with the acetabular trial, the selected tensile forces corresponding to the forces appropriate for proper articular engagement of the femoral component with the acetabular component, and the trial distance corresponding to the required femoral neck length;

a connecting arrangement for connecting the trial femoral head component with the trial femoral stem component, the connecting arrangement being dimensioned and configured for selective movement of the trial femoral head component and the trial femoral stem component relative to one another in the femoral trial, during the trialing procedure, through trial distances relative to one another along a direction of movement corresponding to the predetermined direction of the femoral neck length with the trial femoral head component and the trial femoral stem component connected to one another;

a distance indicator for indicating measured distances corresponding to the trial distances established between the trial femoral head component and the trial femoral stem component along the direction of movement during the trialing procedure; and a force applier dimensioned and configured for coupling with the trial femoral head component and the trial femoral stem component of the femoral trial to apply selected forces urging the trial femoral head component and the trial femoral stem component away from one another and establish the trial distances at measured distances indicated by the distance indicator such that upon coupling of the force applier with the femoral trial and applying the selected forces while the trial femoral head component is engaged with the acetabular trial to urge the trial femoral head component and the trial femoral stem component away from one another and tension the soft tissue during the trialing procedure, a measured distance corresponding to a trial distance at which the selected tensile forces are established in the soft tissue is determined interoperatively, thereby determining interoperatively the femoral neck length required in the femoral component for establishing the forces appropriate for proper articular engagement of the femoral component with the acetabular component.

2. The apparatus of claim 1 wherein the connecting arrangement includes:

a trial femoral neck component for assembly with the trial femoral head component, the trial femoral neck component including a shaft; and a passage in the trial femoral stem component, the passage being dimensioned and configured for receiving the shaft for sliding motion to move the trial femoral head component and the trial femoral stem component relative to one another.

3. The apparatus of claim 1 including:

first and second members for being coupled with the femoral trial such that the trial femoral head component and the trial femoral stem component are moved relative to one another along the direction of movement in response to relative movement between the first and second members along a corresponding direction of movement during the trialing procedure; and a drive mechanism engaged with the first and second members for selectively moving the first and second members relative to one another along the corresponding direction of movement during the trialing procedure;

the measured distances indicated by the distance indicator being distances between the first and second members along the corresponding direction of movement.

4. The apparatus of claim 3 wherein the drive mechanism is configured for selectively moving the first member longitudinally along a linear path relative to the second member.

5. The apparatus of claim 4 wherein the connecting arrangement includes:

a trial femoral neck component for assembly with the trial femoral head component, the trial femoral neck component including a shaft; and a passage in the trial femoral stem component, the passage being dimensioned and configured for receiving the shaft for sliding motion to move the trial femoral head component and the trial femoral stem component relative to one another.

6. The apparatus of claim 5 wherein the first member comprises a first arm having a first engaging face for engaging one of the trial femoral stem component and the trial femoral neck component upon coupling the first member with the femoral trial.

7. The apparatus of claim 6 wherein the second member comprises a second arm having a second engaging face for engaging another of the trial femoral stem component and the trial femoral neck component upon coupling the second member with the femoral trial.

8. The apparatus of claim 7 wherein:

the trial femoral stem component includes a first reference surface for engagement by one of the first engagement face and the second engagement face upon coupling the first member with the femoral trial; and the trial femoral neck component includes a second reference surface for engagement by another of the first engagement face and the second engagement face upon coupling the second member with the femoral trial.

9. The apparatus of claim 8 wherein the second reference surface is integral with and extends laterally across the trial femoral neck component.

10. The apparatus of claim 3 including a frame, and wherein:
the first member includes a first arm affixed to the frame;
the second member includes a second arm mounted on the frame for movement relative to the first arm; and
the drive mechanism is engaged with the second arm for moving the second arm along a longitudinal path relative to the first arm.

11. The apparatus of claim 10 wherein the drive mechanism includes a rack integral with the second arm and extending in a longitudinal direction from the second arm, and a pinion journaled in the frame and engaged with the rack for selective movement of the rack along a linear path to move the second arm along the longitudinal direction relative to the first arm.

12. The apparatus of claim 1 including a force indicator for indicating, during application of the selected forces, the magnitude of selected forces applied at corresponding measured distances indicated by the distance indicator along the direction of movement so as to enable the determination of a measured distance corresponding to an applied force of a selected indicated magnitude.

13. The apparatus of claim 12 including:
first and second members for being coupled with the femoral trial such that the trial femoral head component and the trial femoral stem component are moved relative to one another along the direction of movement in response to relative movement between the first and second members along a corresponding direction of movement during the trialing procedure; and
a drive mechanism engaged with the first and second members for selectively moving the first and second members relative to one another along the corresponding direction of movement during the trialing procedure;
the measured distances indicated by the distance indicator being distances between the first and second members along the corresponding direction of movement.

14. The apparatus of claim 13 wherein the drive mechanism is configured for selectively moving the first member longitudinally along a linear path relative to the second member.

15. The apparatus of claim 14 wherein the connecting arrangement includes:
a trial femoral neck component for assembly with the trial femoral head component, the trial femoral neck component including a shaft; and
a passage in the trial femoral stem component, the passage being dimensioned and configured for receiving the shaft for sliding motion to move the trial femoral head component and the trial femoral stem component relative to one another.

16. The apparatus of claim 15 wherein the first member comprises a first arm having a first engaging face for engaging one of the trial femoral stem component and the trial femoral neck component upon coupling the first member with the femoral trial.

17. The apparatus of claim 16 wherein the second member comprises a second arm having a second engaging face for engaging another of the trial femoral stem component and the trial femoral neck component upon coupling the second member with the femoral trial.

18. The apparatus of claim 17 wherein:
the trial femoral stem component includes a first reference surface for engagement by one of the first engagement face and the second engagement face upon coupling the first member with the femoral trial; and
the trial femoral neck component includes a second reference surface for engagement by another of the first engagement face and the second engagement face upon coupling the second member with the femoral trial.

19. The apparatus of claim 18 wherein the second reference surface is integral with and extends laterally across the trial femoral neck component.

20. The apparatus of claim 13 including a frame, and wherein:
the first member includes a first arm affixed to the frame;
the second member includes a second arm mounted on the frame for movement relative to the first arm; and,
the drive mechanism is engaged with the second arm for moving the second arm along a longitudinal path relative to the first arm.

21. The apparatus of claim 20 wherein the drive mechanism includes a rack integral with the second arm and extending in a longitudinal direction from the second arm, and a pinion journaled in the frame and engaged with the rack for selective movement of the rack along a linear path to move the second arm along the longitudinal direction relative to the first arm.

22. Apparatus for interoperatively determining, during a trialing procedure conducted in connection with total hip arthroplasty at an implant site, a femoral neck length required along a predetermined direction in a femoral component to be engaged with an acetabular component in a prosthetic hip joint to be implanted at the implant site for establishing forces appropriate for proper articular engagement of the femoral component with the acetabular component, the apparatus comprising
a femoral trial for placement at the implant site, the femoral trial including a trial femoral head component and a trial femoral stem component, the femoral neck length being determined by determining a measured distance corresponding to a trial distance between the trial femoral head component and the trial femoral stem component of the femoral trial when the femoral trial is placed at the implant site with the trial femoral head component engaged with an acetabular trial, at which trial distance soft tissue at the implant site is tensioned to establish selected tensile forces in the soft tissue for urging the trial femoral head component into engagement with the acetabular trial, the selected tensile forces corresponding to the forces appropriate for proper articular engagement of the femoral component with the acetabular component, and the trial distance corresponding to the required femoral neck length; and
a connecting arrangement for connecting the trial femoral head component with the trial femoral stem component, the connecting arrangement being dimensioned and configured for selective movement of the trial femoral head component and the trial femoral stem component relative to one another in the femoral trial, during the trialing procedure, through trial distances relative to one another along a direction of movement corresponding to the predetermined direction of the femoral neck length with the trial femoral head component and the trial femoral stem component connected to one another, while the trial femoral head component is engaged with the acetabular trial, to tension the soft tissue and determine, interoperatively, a measured distance corresponding to a trial distance at which the selected tensile forces are established in the soft tissue, thereby determining, interoperatively, the femoral neck length required in the femoral component for establishing the forces appropriate for proper articular engagement of the femoral component with the acetabular component.

23. The apparatus of claim 22 wherein the connecting arrangement includes:
a trial femoral neck component for assembly with the trial femoral head component, the trial femoral neck component including a shaft; and
a passage in the trial femoral stem component, the passage being dimensioned and configured for receiving the shaft for sliding motion to move the trial femoral head component and the trial femoral stem component relative to one another.

24. The apparatus of claim 23 wherein the trial femoral neck component includes a reference surface for engagement to effect selective relative movement between the trial femoral head component and the trial femoral stem component.

25. The apparatus of claim 24 wherein the reference surface is integral with and extends laterally across the trial femoral neck component.

26. A method for interoperatively determining, during a trialing procedure conducted in connection with total hip arthroplasty at an implant site, a femoral neck length required along a predetermined direction in a femoral component to be engaged with an acetabular component in a prosthetic hip joint to be implanted at the implant site for establishing forces appropriate for proper articular engagement of the femoral component with the acetabular component, by determining a measured distance corresponding to a trial distance between a trial femoral head component and a trial femoral stem component of a femoral trial placed at the implant site with the trial femoral head component engaged with an acetabular trial, at which trial distance soft tissue at the implant site is tensioned to establish selected tensile forces in the soft tissue for urging the trial femoral head component into engagement with the acetabular trial, the selected tensile forces corresponding to the forces appropriate for proper articular engagement of the femoral component with the acetabular component, and the trial distance corresponding to the required femoral neck length, the method comprising:
connecting the trial femoral head component with the trial femoral stem component for selective movement relative to one another in the femoral trial, during the trialing procedure, along a direction of movement corresponding to the predetermined direction of the femoral neck length;
applying selected forces for selectively moving the trial femoral head component and the trial femoral stem component relative to one another among trialing distances along the direction of movement, while the trial femoral head component is engaged with the acetabular trial during the trialing procedure; and
measuring distances corresponding to the trialing distances to determine a measured distance corresponding to a trialing distance at which an applied selected force tensions the soft tissue to establish the selected tensile forces in the soft tissue, thereby determining interoperatively the femoral neck length required in the femoral component for establishing the forces appropriate for proper articular engagement of the femoral component with the acetabular component.

27. The method of claim 26 including measuring, during the trialing procedure, magnitudes of applied forces urging the trial femoral head component and the trial femoral stem component away from one another at corresponding measured distances such that a measured distance corresponding to the trialing distance at which the selected tensile forces are established in the soft tissue is determined by an applied force of a selected magnitude.

28. The method of claim 27 including:
coupling first and second members for movement relative to one another with relative movement of the trial femoral head component and the trial femoral stem component; and
providing first and second reference surfaces on corresponding first and second members such that the measured distances are measured between the reference surfaces of the first and second members.

29. The method of claim 26 wherein the selective movement of the trial femoral head component and the trial femoral stem component relative to one another is along a linear path.

* * * * *